(12) United States Patent
Li et al.

(10) Patent No.: US 7,831,015 B2
(45) Date of Patent: Nov. 9, 2010

(54) COMBINING X-RAY AND ULTRASOUND IMAGING FOR ENHANCED MAMMOGRAPHY

(75) Inventors: Baojun Li, Waukesha, WI (US); Jean-Baptiste Thibault, Milwaukee, WI (US); Anne Lindsay Hall, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 44 days.

(21) Appl. No.: 12/415,637

(22) Filed: Mar. 31, 2009

(65) Prior Publication Data

US 2010/0246760 A1    Sep. 30, 2010

(51) Int. Cl.
*A61B 6/04* (2006.01)
*A61B 8/00* (2006.01)

(52) U.S. Cl. .................................. 378/37; 600/437
(58) Field of Classification Search ............ 378/37, 378/63, 195, 208; 600/437–461
See application file for complete search history.

(56) References Cited

U.S. PATENT DOCUMENTS

| | | | |
|---|---|---|---|
| 5,437,278 A | | 8/1995 | Wilk |
| 5,664,573 A | * | 9/1997 | Shmulewitz ............ 600/445 |
| 6,447,451 B1 | | 9/2002 | Wing et al. |
| 6,475,146 B1 | | 11/2002 | Frelburger et al. |
| 6,480,565 B1 | | 11/2002 | Ning |
| 6,497,661 B1 | | 12/2002 | Brock-Fisher |
| 6,775,404 B1 | | 8/2004 | Pagoulatos et al. |
| 6,795,571 B2 | | 9/2004 | Kusch |
| 6,980,419 B2 | | 12/2005 | Smith et al. |
| 6,987,831 B2 | | 1/2006 | Ning |
| 7,115,093 B2 | | 10/2006 | Halmann et al. |

(Continued)

FOREIGN PATENT DOCUMENTS

EP    1643444    5/2006

(Continued)

OTHER PUBLICATIONS

Pagoulatos, et al., Interactive 3-D Registration of Ultrasound and Magnetic Resonance Images Based on a Magnetic Position Sensor, IEEE Transactions on Information Technology in Biomedicine, vol. 3, No. 4, Dec. 1999, p. 278-288.

(Continued)

*Primary Examiner*—Hoon Song (57) ABSTRACT

A mammography system includes a patient support with a breast opening. Beneath the patient support, an x-ray source transmits x-rays through a breast of a patient extending through the opening. An opposing x-ray detector receives the x-rays to obtain an x-ray image of the breast. The x-ray source and x-ray detector rotate around the opening while maintaining a fixed relation relative to one another, and a container is filled with a fluid and positioned proximate to and aligned with the opening to receive the breast. An ultrasound transmitter transmits sound waves through the breast when positioned within the fluid. An opposing ultrasound receiver receives the sound waves to obtain an ultrasound image of the breast. In a preferred embodiment, the mammography system positions the ultrasound transmitter and/or ultrasound receiver at a first position when obtaining the x-ray image of the breast and a second position when obtaining the ultrasound image of the breast. In other preferred embodiments, mammography methods correspond thereto.

31 Claims, 7 Drawing Sheets

U.S. PATENT DOCUMENTS

| | | | |
|---|---|---|---|
| 7,412,027 B2 | 8/2008 | Yakubovsky et al. | |
| 2002/0131551 A1* | 9/2002 | Johnson et al. | 378/62 |
| 2003/0007598 A1* | 1/2003 | Wang et al. | 378/37 |
| 2004/0150963 A1 | 8/2004 | Holmberg et al. | |
| 2004/0236206 A1 | 11/2004 | Sakas et al. | |
| 2005/0049497 A1 | 3/2005 | Krishnan et al. | |
| 2005/0251035 A1 | 11/2005 | Wong et al. | |
| 2005/0288581 A1 | 12/2005 | Kapur et al. | |
| 2006/0030768 A1 | 2/2006 | Ramamurthy et al. | |
| 2006/0034508 A1 | 2/2006 | Zhou et al. | |
| 2006/0116578 A1 | 6/2006 | Grunwald et al. | |
| 2006/0136259 A1 | 6/2006 | Weiner et al. | |
| 2006/0155577 A1 | 7/2006 | Niemeyer | |
| 2006/0173303 A1 | 8/2006 | Yu et al. | |
| 2006/0264749 A1 | 11/2006 | Weiner et al. | |
| 2007/0016442 A1 | 1/2007 | Stroup | |
| 2007/0168308 A1 | 7/2007 | Wang et al. | |
| 2007/0237371 A1 | 10/2007 | Zhu et al. | |
| 2008/0009724 A1 | 1/2008 | Lee et al. | |
| 2008/0218743 A1 | 9/2008 | Stetten et al. | |
| 2008/0219540 A1 | 9/2008 | Ter Mors | |
| 2008/0221478 A1* | 9/2008 | Ritchie et al. | 600/562 |
| 2008/0249415 A1* | 10/2008 | Okamura et al. | 600/445 |
| 2009/0290679 A1* | 11/2009 | Mikami et al. | 378/37 |

FOREIGN PATENT DOCUMENTS

| | | |
|---|---|---|
| WO | WO2006111871 | 2/2006 |
| WO | WO2006111874 | 2/2006 |
| WO | WO2007133143 | 11/2007 |

OTHER PUBLICATIONS

Chen et al., Cone-beam volume CT mammographic imaging: feasibility study, Proceedings of SPIE vol. 4320, 655 (2001), DOI:10.1117/12.430894.

Boone PhD et al., Dedicated Breast CT: Radiation Dose and Image Quality Evaluation, Radiology 2001, 221: 657-667.

* cited by examiner

COMBINING X-RAY AND ULTRASOUND IMAGING FOR ENHANCED MAMMOGRAPHY

BACKGROUND

In general, the inventive arrangements relate to systems and methods for mammography, and more specifically, to combining x-ray imaging techniques and ultrasound imaging techniques to provide an integrated, enhanced solution for breast cancer screenings and/or the like.

With approximately 50,000 deaths each year, breast cancer is one of the leading causes of death of women in the U.S.A. However, if breast cancer is detected at an early stage (e.g., micro-calcifications of less than 10 mm in diameter or so), then sixteen year survival rates can exceed 90% or better. In addition, clusters of micro-calcifications of 1 mm or less often precede the onset of breast carcinoma, which can indicate a potential site of a cancerous lesion. Accordingly, the clinical goal of breast imaging is to detect abnormalities, tumor masses, and/or the like, particularly when they are as small as possible—and thus, early detection of any signs of breast cancer are of paramount importance to the overall well-being, and survival, of many patients around the world.

Referring generally, there are two basic types of tests that can be used to detect breast cancer and/or other breast abnormalities. The first type of tests are early screening tests, such as an annual mammogram, which can be routinely conducted every year or so even though there may not yet be any hint and/or suspicion of an abnormality in the patient's breast. Instead, such early screening tests can be conducted in order to begin to uncover any early, unsuspected stages of breast cancer and/or the like. The second type of tests, on the other hand, are diagnostic tests, which can be conducted whenever there is a hint and/or suspicion of an abnormality in the patient's breast, such as, for example, when detected by the early screening test and/or experienced symptoms by the patient. Such diagnostic tests are usually conducted in order to start to, or to continue to gather, additional information about the breast and/or its condition.

Accordingly, mammography is an effective imaging technique by which a patient's breast/breasts is/are non-invasively examined and/or screened in order to detect abnormalities, such as lumps, fibroids, lesions, calcifications, micro-calcifications, and/or the like.

Many mammography techniques use x-ray imaging systems. Common x-ray imaging systems often include, for example, a source of x-ray radiation, such as an x-ray source, and an x-ray detector to obtain an x-ray image of the breast. Another common type of x-ray imaging system used in mammography involves cone beam computed tomography (CT), in which a patient lies prone on a patient support, such as an examination table, containing one or more breast holes through which a breast downwardly extends, particularly while a gantry frame then rotates the x-ray source and x-ray detector around the breast such that the breast lies within a cone beam of x-ray radiation generated by the CT system. Such a rotational frame system enables a caregiver to collect multiple x-ray projections of the patient's breast at many different viewing angles. In any event, x-ray imaging is often effective at characterizing, for example, benign and cancerous structures embedded in breast tissue, such as calcifications and/or masses.

Other common mammography techniques use ultrasound imaging systems. Common ultrasound imaging systems often include, for example, a source of sound waves, such as an ultrasound transmitter, and an ultrasound receiver to obtain an ultrasound image of the breast. Since sound is a wave and requires a medium through which to travel (e.g., a tissue and/or a liquid), many ultrasound imaging systems use an ultrasonic coupling gel and/or paste to ensure proper communication between the ultrasound probe and the object being imaged. Ultrasound gels, for example, typically ensure good transmission of acoustic energy, including in ultrasound mammography imaging systems. In any event, ultrasound imaging is often effective at differentiating, for example, benign verses malignant cysts and/or masses, as well as cystic verses solid lesions, etc.

Now then, with multi-modality mammography imaging systems, x-ray imaging systems and ultrasound imaging systems, for example, can be combined to enhance and/or co-register acquired breast imagery, particularly with a patient in a single, or virtually single, position within a single examination session, thereby leveraging the respective strengths of the various imaging techniques. For example, an ultrasound image may show a lesion that might not have been otherwise visible with an x-ray image—particularly, for example, in women with dense breasts. Accordingly, both x-ray imaging systems and ultrasound imaging systems have unique advantages, which are both well-suited to mammography and can facilitate early detection of breast cancer. It is, therefore, advantageous to combine x-ray imaging systems and ultrasound imaging systems in order to enhance early screening and diagnostic capabilities. Such combined systems can provide enhanced sensitivity and specificity, as well as decreasing patient inconvenience, increasing patient comfort, and/or increasing workflow productivity. As a result, for example, an x-ray imaging system can be used for an initial screening, and if an abnormality is detected and/or suspected, then an ultrasound imaging system can be used to further the diagnosis—all within a single examination session and/or without requiring a patient to move between different medical imaging systems.

While there have been several previous attempts to couple multiple modality systems for enhanced mammography, successfully combining the respective imaging systems raises, for example, many difficulties in physically mounting the systems in order to be able to effectively operate such a combined system and obtain useful patient information therefrom. In addition, it remains desirable to combine x-ray imaging systems and ultrasound imaging systems in such a way that each system can still be used independently and/or in a combined fashion, particularly as needed and/or desired.

SUMMARY

In one embodiment, a mammography system includes a patient support with a breast opening therein. Beneath the patient support, an x-ray source is configured to transmit x-rays through a breast of a patient extending through the opening. An opposing x-ray detector is configured to receive the x-rays to obtain an x-ray image of the breast. The x-ray source and x-ray detector rotate around the opening while maintaining a fixed relation relative to one another, and a container is filled with a fluid and positioned proximate to and aligned with the opening to receive the breast. An ultrasound transmitter is configured to transmit sound waves through the breast when positioned within the fluid. An opposing ultrasound receiver is configured to receive the sound waves to obtain an ultrasound image of the breast.

In another embodiment, the mammography system positions the ultrasound transmitter and/or ultrasound receiver at a first position when obtaining the x-ray image of the breast and a second position when obtaining the ultrasound image of the breast.

In other embodiments, mammography methods correspond thereto.

These and other features and advantages of the inventive arrangements will become more readily apparent from the following detailed description taken in conjunction with the drawings and/or claims contained herein.

DETAILED DESCRIPTION

Referring now generally to FIGS. 1-4, a mammography system 10 comprises a patient support 12 having at least one opening 14 therein, such that at least a portion of a patient's 16 breast 18 extends, at least in part, through the opening 14. More specifically, the patient support 12 is preferably an examination table that supports the patient 16 and in which the patient 16 lies prone thereon such that the patient's 16 breast 18 to be imaged extends through a suitably-sized breast hole, such as the opening 14 in the patient support 12. With the patient 16 lying face down on the patient support 12, the patient's 16 breast 18 preferably extends downward through the opening 14, preferably assisted by the downward pull of gravity. Ideally, a hollowed, or at least partially hollowed, chamber 20 is formed on an opposing side of the patient support 12, such as underneath the patient support 12 when the patient support 12 extends horizontally, or at least approximately horizontally, with a floor surface FS. As such, the patient's 16 breast 18 extends, at least in part, through the opening 14 in the patient support 12 and, at least in part, into the hollowed chamber 20 on the opposing side thereof.

Figure 1:
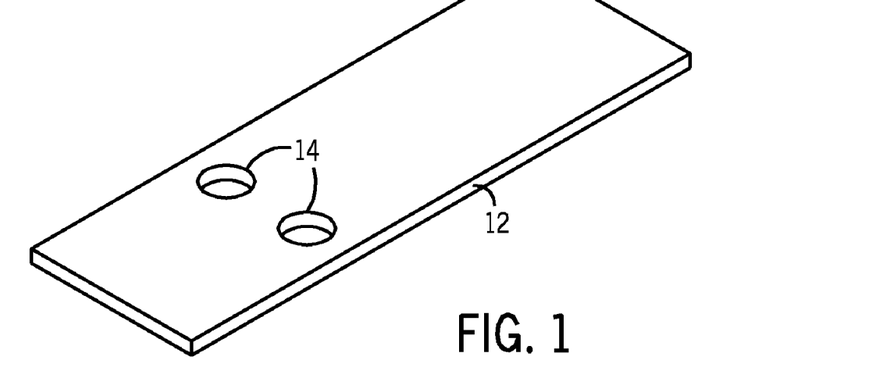
FIG. 1 is a perspective view of a patient support.
Figure 2:
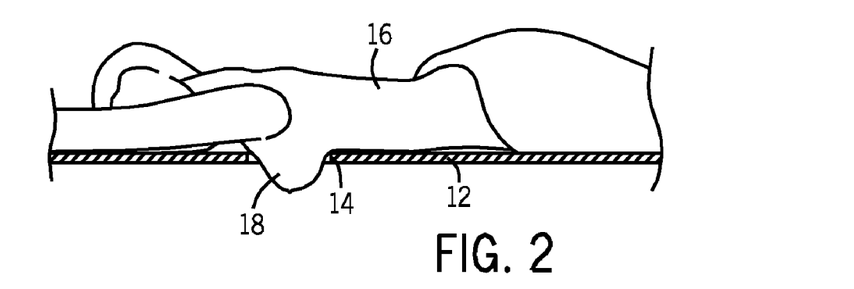
FIG. 2 is a partial side view of a patient supported on the patient support of FIG. 1.
Figure 3:
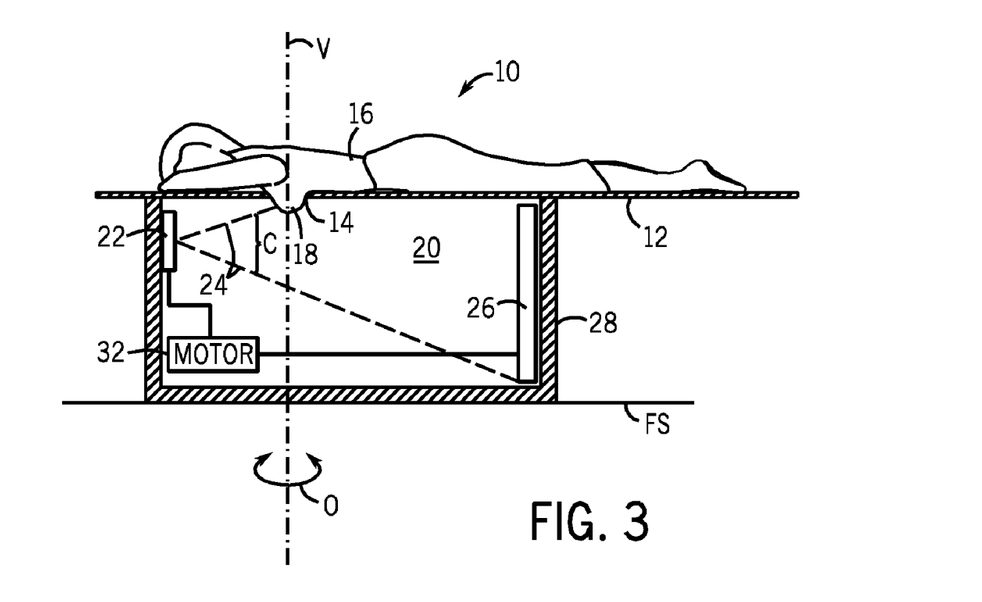
FIG. 3 is a combined side and partial perspective schematic view of a cone beam computed tomography (CT) x-ray imaging system.
Figure 4:
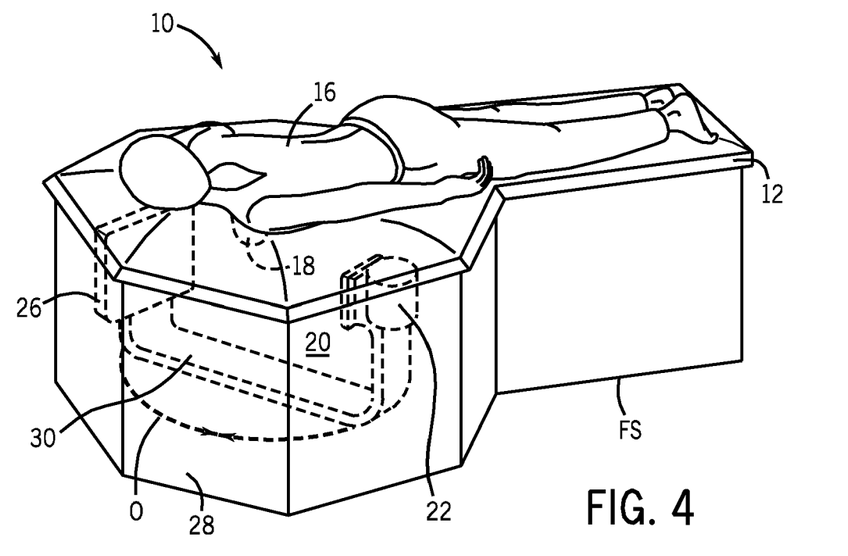
FIG. 4 is an elevated perspective view of the cone beam CT x-ray imaging system of FIG. 3.
Figure 5:
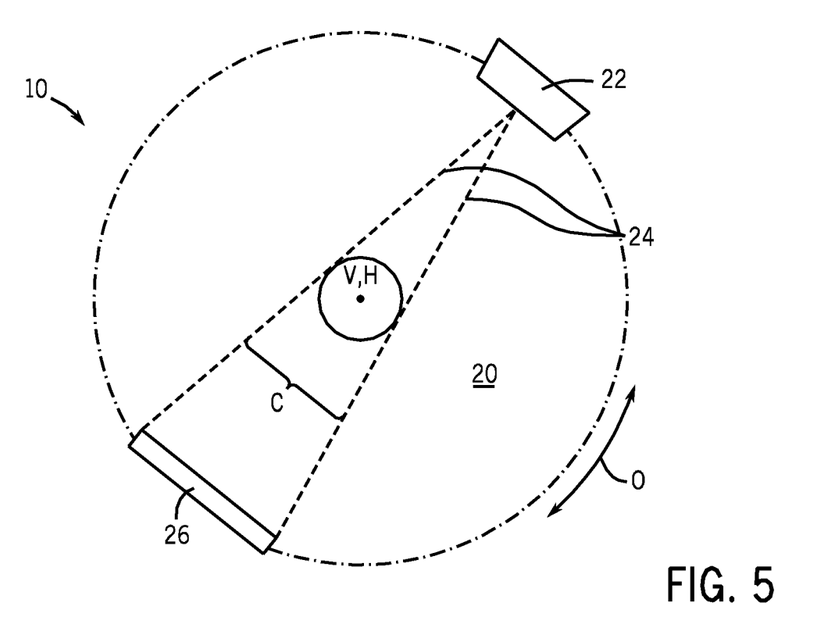
FIG. 5 is a simplified, conceptual view of a CT x-ray imaging system.

Referring now generally to FIGS. 3-5, an x-ray source 22 within the hollow chamber 20 provides a stream of x-ray radiation such that x-rays 24 pass through the patient's 16 breast 18 and are received by an opposing x-ray detector 26 configured to receive same. As depicted, a gantry 28 ideally surrounds and forms the hollow chamber 20, while a common support 30 supports the x-ray source 22 and x-ray detector 26, particularly on opposing sides of the opening 14 on a same side of the patient support 12.

Ideally, the common support 30 is actuated and/or turned by a motor 32 and/or the like operating in conjunction therewith, preferably within the hollow chamber 20 of the gantry 28, so as to be rotable around a vertical (or nearly so) axis V relative to the opening 14. Accordingly, the x-ray source 22 and x-ray detector 26 ideally travel about an orbit O such that the patient's 16 breast 18 remains in the path of a cone bone C created by the x-rays 24 so as to produce an x-ray image of at least that portion of the breast 18 extending through the opening 14 in the patient support 12. As such, the ratable common support 30 enables the mammography system 10 to collect multiple x-ray projections of the breast 18 at different viewing angles, thereby comprising a cone beam computed tomography (CT) x-ray imaging system, as well-known in the art. As described, the relative positions of the x-ray source 22 and/or x-ray detector 26 remain geometrically fixed relative to one another. In addition, either one of the patient's 16 breasts 18 can be moved into the imaging field and scanned first, followed by the other breast 18, or the patient's 16 two breasts 18 can also be scanned together.

Figure 6:
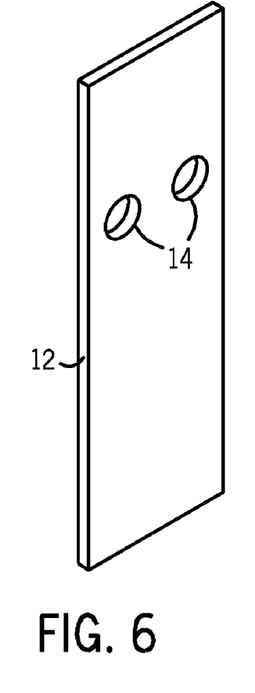
FIG. 6 is an alternative perspective view of a patient support.
Figure 7:
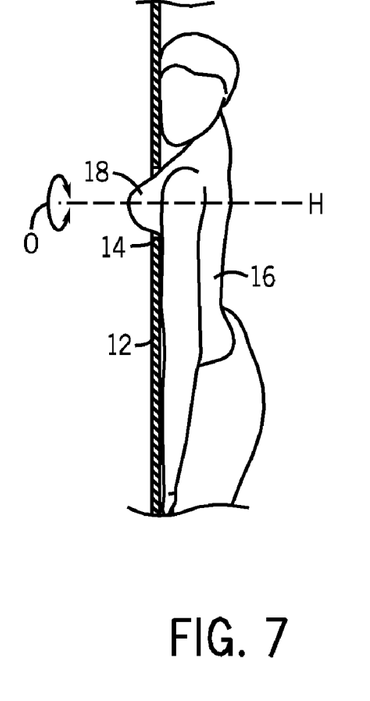
FIG. 7 is a partial side view of a patient supported by the patient support of FIG. 6.
Figure 8:
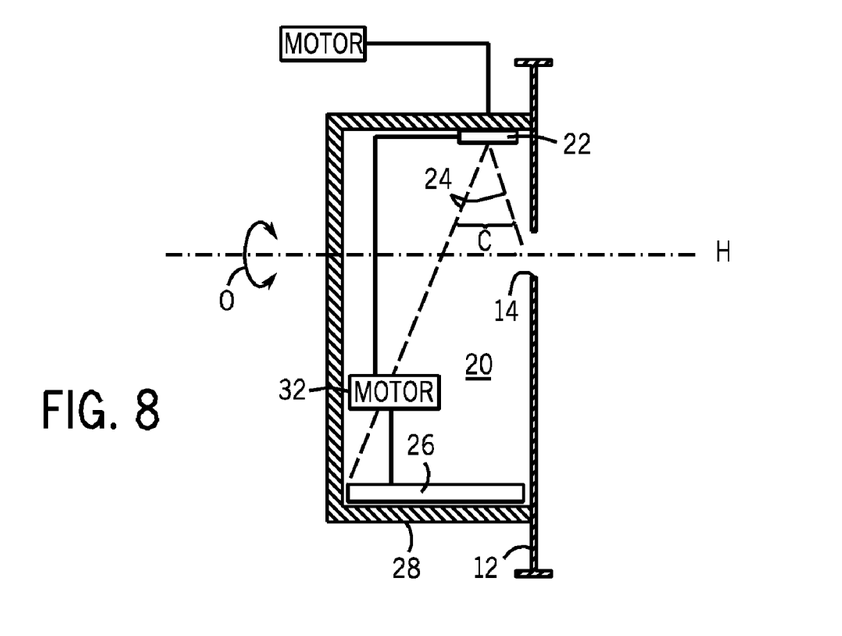
FIG. 8 is a simplified conceptual side-view of a CT x-ray imaging system used in conjunction with FIGS. 6-7.
Figure 9:
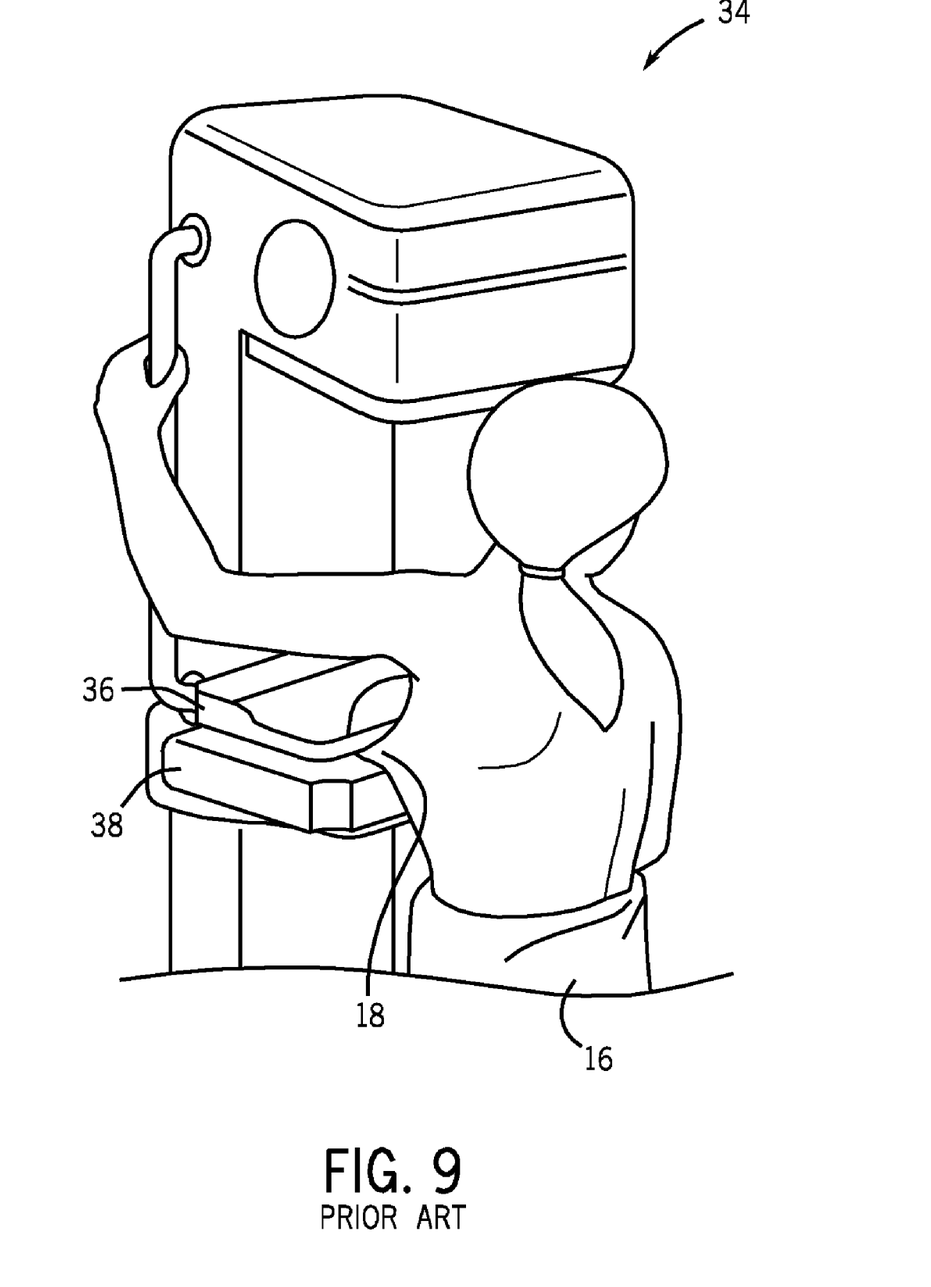
FIG. 9 is a perspective view of a conventional digital mammography system.

As described, the patient's 16 breast 18 ideally descends through the opening 14 in the patient support 12. As such, and as generally shown in FIGS. 6-8, the mammography examination can also be performed while the patient 16 sits or stands erect. More specifically, the opening 14 in the patient supports 12 still receives the patient's 16 breast 18, and the gantry 28—including the common support 30 holding the x-ray source 22 and/or x-ray detector 26—is thereby oriented to rotate about a horizontal (or nearly so) axis H as opposed to the vertical axis V of several of the other figures so as to form the orbit O. In other respects, however, the mammography systems 10 of FIGS. 6-8 operate as do the mammography systems 10 of the other figures. In contradistinction, a conventional mammography system 34 is shown in FIG. 9, in which the patient's 16 breast 18 is instead inserted between two (or more) compression surfaces 36, 38 (e.g., plates). As such, the compression surfaces 36, 38 maintain the position of, and compress, the breast(s) 18 during examination. Such conventional mammography systems 34 can cause patient 16 discomfort (e.g., pain), particularly as opposed to the patient support 12 of the inventive arrangements, which are ideally more comfortable for the patients 16 when compared to conventional flattening and/or hard breast compression examination techniques.

Figure 10:
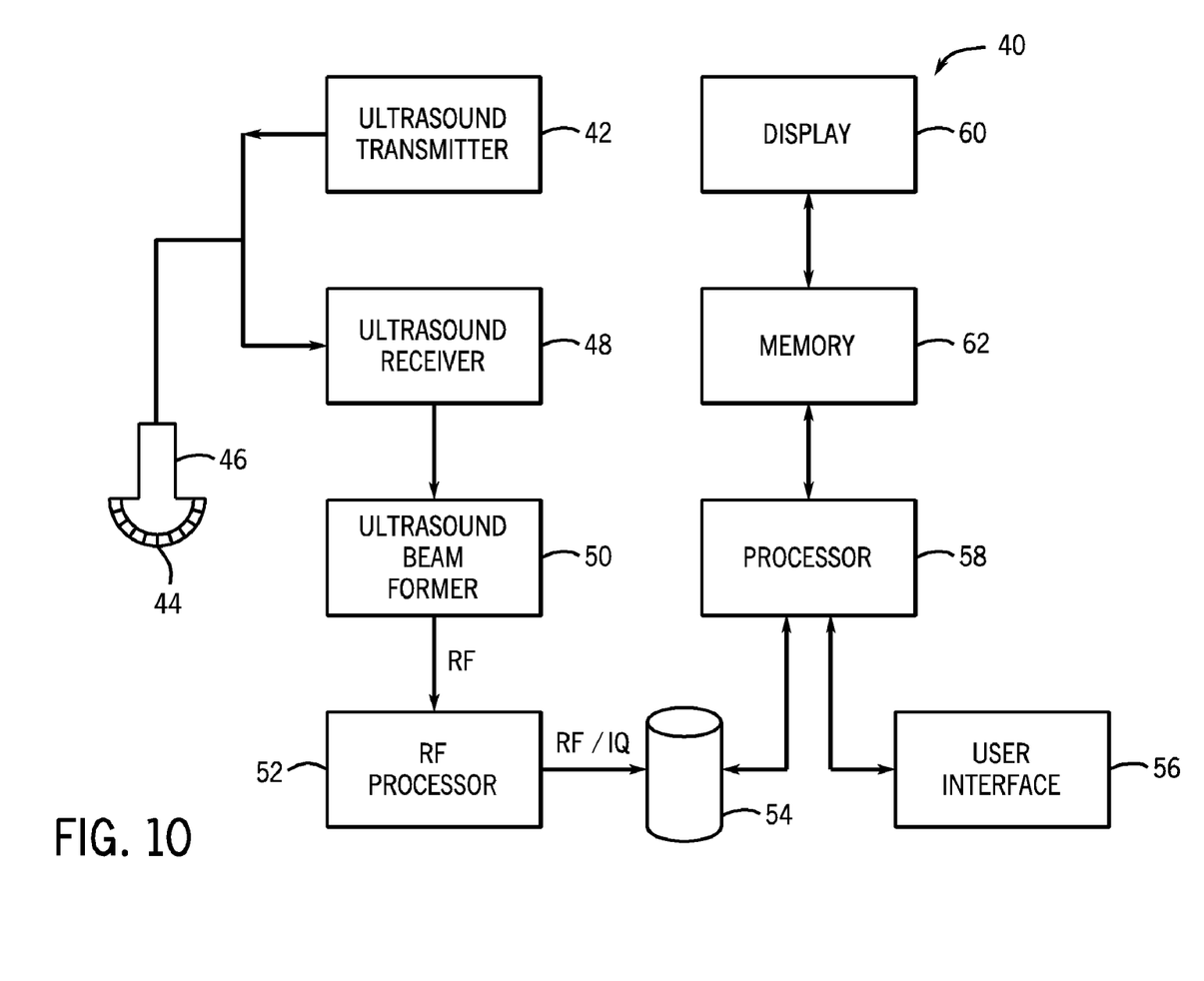
FIG. 10 is a block diagram view of an ultrasound imaging system.

Referring now to FIG. 10, an ultrasound system 40 is depicted. More specifically, the ultrasound system 40 includes an ultrasound transmitter 42 that drives transducers 44 within an ultrasound probe 46 to emit ultrasonic signals into an object, such as the patient's 16 breast 18 (not shown in FIG. 10). A variety of geometries may be used for the ultrasound system 40. For example, in operation, the ultrasound system 40 may acquire data sets by various techniques (e.g., freehand scanning, scanning using transducers 44 having position sensors, scanning using a 2D or matrix array, 3D scanning, real-time 3D scanning, volume scanning, 4D scanning, etc.), particularly by moving the transducers 44 along a linear and/or arcuate path while scanning a region of interest, which may be moved manually, mechanically, electronically, and/or by any various combinations thereof.

In any event, the transmitted ultrasonic signals are back-scattered from the object, such as breast 18 tissue (not shown in FIG. 10), to produce echo signals that return to the transducers 44. These echo signals are then received by an ultrasound receiver 48 in communication with the transducers 44.

These echo signals are then passed from the ultrasound receiver 48 to an ultrasound beamformer 50, which performs beamforming and outputs RF signal data therefrom. The RF signal data then passes from the ultrasound beamformer 50 to an RF processor 52. In an optional embodiment, the RF processor 52 may also include a complex demodulator (not shown) that demodulates the RF signal data to form IQ data pairs that represent the echo signals. Either the RF signal data or IQ data pairs are then routed from the RF processor 52 to a RF/IQ buffer 54 for temporary storage. A user interface 56 can also be used to control operation of the ultrasound system 40, including, for example, controlling input of patient data, changing a scanning or display parameter, and/or the like.

Preferably, the ultrasound system 40 also includes a processor 58 to process the acquired ultrasound information (e.g., the RF signal data or IQ data pairs) from the RF/IQ buffer 54 and prepare frames of ultrasound information for display on a display 60. Preferably, the processor 58 is configured to perform one or more processing operations according to selectable functions performed on the acquired ultrasound information. For example, the acquired ultrasound information can be processed in real-time during a scanning session as the echo signals are received; additionally, and/or alternatively, the acquired ultrasound information can also be stored temporarily in the RF/IQ buffer 54 (or other) during a scanning session, and then processed in other than real-time in a live or off-line operation.

In a preferred embodiment, the ultrasound system 40 continuously acquires ultrasound information at a frame rate in excess of, for example, fifty frames per second, which is approximately the perception rate of the human eye. Thus, the acquired ultrasound information can be displayed on the display 60 at a slower frame-rate. Accordingly, a memory 62 may also be provided between the processor 58 and the display 60 for storing processed frames of the acquired ultrasound information that are not yet ready and/or needed for immediate display on the display 60. In an exemplary embodiment, for example, the memory 62 is of sufficient capacity to store at least several seconds worth of processed frames of the acquired ultrasound information. Preferably, these frames of information are stored in a manner that facilitates their later retrieval according to an order and/or time and/or other of acquisition, and the memory 62 may comprise any known data storage medium.

Figure 14:
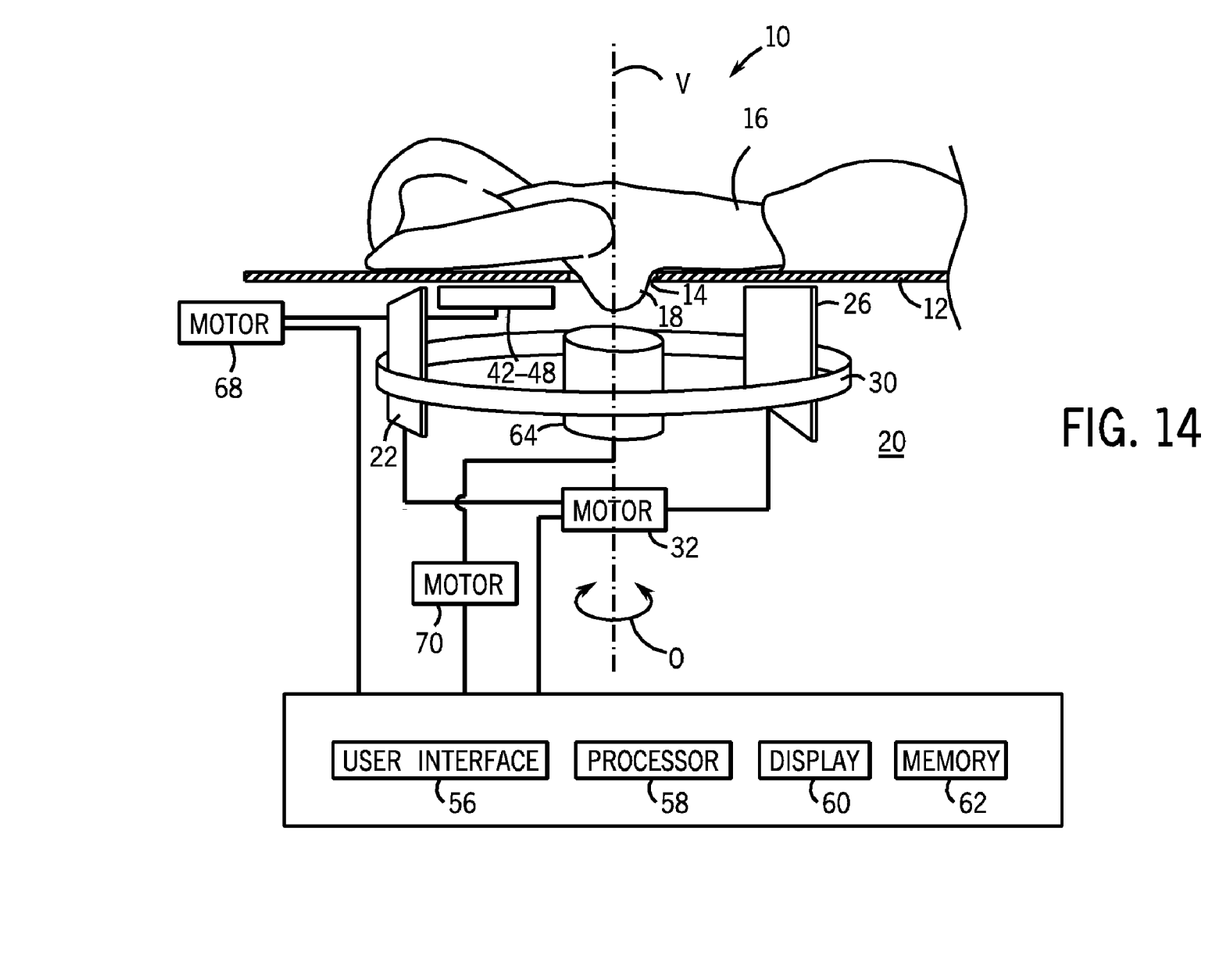

Now then, as shown in FIG. 14, the user interface 56, processor 58, display 60, and/or memory 62 may also be utilized by the x-ray imaging systems 10 of the other figures. For example, they may be used to control operation of the x-ray source 22 and/or x-ray detector 26, as well as the ultrasound system 40.

Referring now generally to FIGS. 11-14, there are shown partial side and conceptual views of mammography systems 10 comprising an x-ray imaging system and an ultrasound imaging system according to the inventive arrangements. More specifically, for example, the x-ray imaging systems (e.g., the x-ray sources 22 and/or x-ray detectors 26) can be used to conduct screening tests, while the ultrasound systems (e.g., the ultrasound transmitters 42 and ultrasound receivers 48) can be used to conduct diagnostic tests. Accordingly, for example, the patient support 12 has an opening 14 therein such that the patient 16 lies face down on the patient support 12 such that the patient's 16 breast 18 extends downwardly through the opening 14. The patient's 16 breast 18 is therefore available for both x-ray imaging and ultrasound imaging.

Now then, the following arrangements will be described with respect to the scanning of a single breast 18 for clarity. However, as previously described, the patient support 12 may have also have two openings 14 therein so that both of the patient's 16 breasts 18 can be examined simultaneously.

Accordingly, an approximately breast-sized container 64 is positioned underneath the opening 14 in close proximity to the patient support 12 such that the breast 18 of the patient 16 that extends downwardly is thus positioned within the container 64 and submerged in a fluid 66 within the container 64. Ideally, the fluid 66 is water or another liquid or gel, such as soundwave conductive fluid or gel, which is particularly conductive to ultrasound imaging. Preferably, the container 64 is positioned within the chamber 20 of the gantry 28 beneath the patient support 12. Preferably, it aligns with the opening 14 in the patient support 12, preferably about the vertical axis V or horizontal axis H.

The x-ray source 22 is also positioned beneath the patient support 12, and it emits the x-rays 24 that pass through the patient's 16 breast 18 and are received by the x-ray detector 26 configured to receive same. As previously described, the x-ray source 22 and x-ray detector 26 can be rotably mounted in tandem such that they can be rotated with respect to the breast 18 in order to scan the breast 18 at different viewing angles.

In addition, the ultrasound probe 46 is located in close proximity to the container 64 such that the ultrasound probe 46 includes, as is conventional, the ultrasound transmitter 42 and/or ultrasound receiver 48. In addition, the ultrasound probe 46 may also comprise multiple ultrasound probes 46 within the chamber 20 of the gantry 28 and/or one or more multiple ultrasound probes 46 built in the shape of, for example, a ring around the opening 14 (not shown).

In one embodiment, the ultrasound probe 46 is movable with respect to the container 64 and oriented so as to introduce sound waves into the container 64 to penetrate the patient's 16 breast 18 when submerged within the fluid 66 within the container 64. The ultrasound probe 46 receives sound waves reflected from tissue within the breast 18 being scanned so as to create an image of the breast 18 that can be analyzed in a conventional manner to provide information as to any abnormalities therewithin the patient's 16 breast 18.

Figure 11:
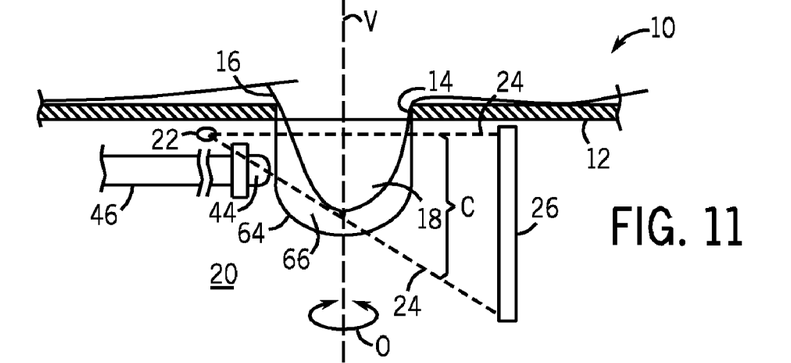
FIGS. 11-14 are partial side and conceptual views of mammography systems comprising an x-ray imaging system and an ultrasound imaging system according to the inventive arrangements.

As such, it can now be seen that the inventive arrangements allow the use of the cone beam computed tomography (CT) x-ray imaging system, as well the ultrasound imaging system, particularly for cancer screening and/or diagnosis of an abnormality of the patient's 16 breast 18. With the inventive techniques, either the x-ray imaging system and/or ultrasound imaging system can be used separately, exclusive of the other, or, in a preferred embodiment, together. For example, the x-ray imaging system can be used initially for screening the patient 16 for abnormalities, and the ultrasound imaging system can then be used to carry out diagnostic tests, either during the same visit by the patient 16 or at a later time. Accordingly, as shown in FIG. 11, for example, both the x-ray imaging system (e.g., the x-ray sources 22 and/or x-ray detectors 26) and ultrasound system (e.g., the ultrasound transmitters 42 and ultrasound receivers 48) are combined in a single mammography system 10 according to the inventive arrangements.

As needed and/or desired, the imaging results of each system can be displayed on the display 60 separately and/or in a correlated/registered fashion.

Figure 12:
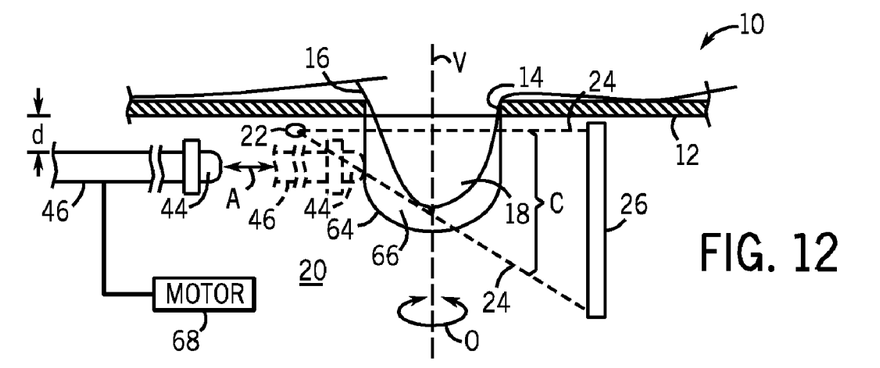

Referring now generally to FIG. 12, there is an alternate embodiment of the inventive arrangements. More specifically, with this embodiment, the ultrasound probe 46 is movably mounted with respect to the container 64 such that it can be moved to and from i) a first position displaced away from the container 64, that is, in a retracted position, as illustrated by the solid line position of the ultrasound probe 46 in the figure, and ii) a second position proximate the container 64, that is, in an operative and/or engaged position, as illustrated by the dashed line position of the ultrasound probe 46 in the figure, whereby the ultrasound probe 46 is sufficiently close to or touching the container 64 so as to be able to effectively emit the sound waves into the container 64 and penetrate the patient's 16 breast 18 when obtaining the ultrasound image in the second position. Thus, the ultrasound probe 46 is in its retracted position when the mammography system 10 is obtaining the x-ray image of the breast 18, thereby being free from interfering therewith, and in its operative position when the mammography system 10 is obtaining the ultrasound image of the breast 18. An arrow A representatively depicts movement of the ultrasound probe 46 in this fashion—e.g., towards and away from the container 64.

A motor 68 and/or the like can direct the ultrasound probe 46 between its first (e.g., retracted) and second (e.g., operative) positions, as needed and/or desired, or it can also be move manually as well, including along a track (not shown) and/or the like.

By using a movable ultrasound probe 46, it can be moved out of the way of the x-ray source 22 and x-ray detector 26 (e.g., to its retracted position) whenever the x-ray source 22 and x-ray detector 26 are rotated about the patient's 16 breast 18 to screen the different sections thereof. Accordingly, the ultrasound probe 46 is also not in the way of the x-rays 24 when the x-ray source 22 and x-ray detector 26 are operative within the mammography system 10 to obtain the x-ray image. This removes the ultrasound probe 46 from the cone beam of x-rays 24 fanning between the x-ray source 22 and x-ray detector 26, particularly as the ultrasound probe 46 may contain metal wires, microchips, and/or other numerous components that can interfere with obtaining an optimal x-ray image (e.g., causing saturated streaks, bandings, etc. that can otherwise cross the x-ray imaging field of view). However, by moving the ultrasound probe 46 between a position proximate the breast 18 when obtaining the ultrasound image and a position displaced from the breast 18 when obtaining the x-ray image, the x-ray source 22 and x-ray detector 26 operate free from interference thereof, thereby, for example, improving image quality. As a result, the ultrasound probe 46 is withdrawn from the x-ray field of view when not in use for ultrasound imaging.

Figure 13:
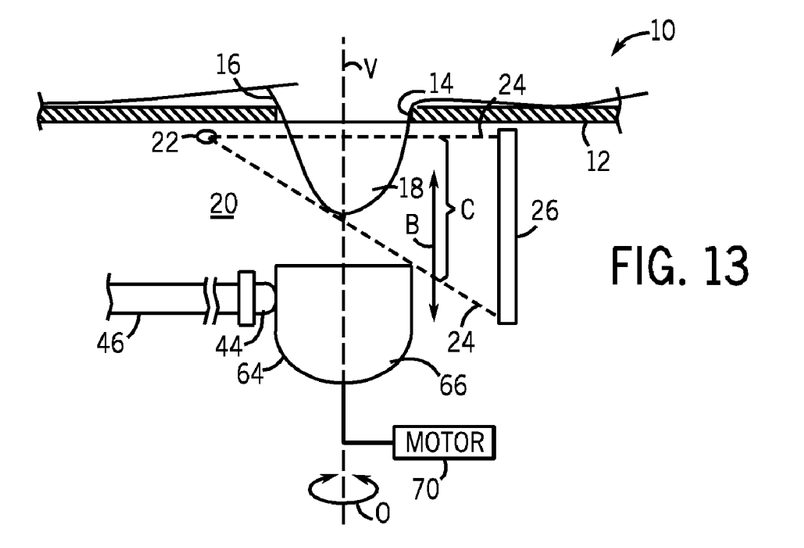

Referring now generally to FIG. 13, there is an alternate embodiment of the inventive arrangements. More specifically, with this embodiment, the container 64 is additionally and/or alternatively movable with respect to the opening 14. For instance, as previously described, the container 64 is positioned underneath the opening 14 in close proximity to the patient support 12 such that the breast 18 of the patient 16 that extends downwardly is thus able to be positioned within the container 64. It too is moveable between multiple positions to bring the container 64 towards and/or away from the patient support 12 and/or opening 14. More specifically, with this embodiment, the container 64 is movably mounted with respect to, for example, the opening 14 within the patient support 12, such that it can be moved from i) a first position displaced away from the opening 14, that is, in a retracted position, and ii) a second position proximate the opening 14, that is, in an operative and/or engaged position, whereby the container 64 is sufficiently moveable close to or touching the patient support 12 to receive the patient's 16 breast 18 when the patient's 16 breast 18 is positioned within the opening 14 and an ultrasound image is desired. Thus, the container 64 is in its retracted position when the mammography system 10 is obtaining the x-ray image of the breast 18, thereby being generally free from interfering therewith, and in its operative position when the mammography system 10 is obtaining the ultrasound image of the breast 18. An arrow B representatively depicts movement of the container 64 in this fashion—e.g., towards and away from the patient support 12 and/or opening 14.

A motor 70 and/or the like can direct the container 64 between its first (e.g., retracted) and second (e.g., operative) positions, as needed and/or desired, or it can also be move manually as well, including along a track (not shown) and/or the like.

In addition, the ultrasound probe 46 can maintain a fixed position relative to the container 64 (see, e.g., FIGS. 11 and 13) such that it is not required to physically couple the ultrasound probe 46 to the container 64 every time the ultrasound system 40 is to be used.

Ideally, both of the embodiments depicted in FIGS. 12-13 can also be implemented individually and/or in a combined fashion. For example, in one embodiment, the ultrasound probe 46 could move up and down along with the container 64 towards and away from the patient support 12, as shown by arrow B in FIG. 13, or, in an additional and/or alternative embodiment, it could remain stationary with respect to a fixed distance d from the patient support 12, as shown in FIG. 12, all the while moving towards and away from the container 64, as shown by arrow A in FIG. 12.

When the container 64 is in a retracted position with respect to the patient support 12 (see, e.g., FIG. 13), the patient's 16 breast 18 is no longer immersed in the fluid 66 contained within the container 64. Again, the motor 70 preferably moves the container 64 between its operative position for ultrasound imagery and its retracted position for x-ray imagery, particularly free from interference thereof. Accordingly, when obtaining an ultrasound image of the patient's 16 breast 18, the ultrasound probe 46 is retracted so that the x-rays 24 that pass from through the patient's 16 breast 18 do not also pass through any or all of the container 64 and/or fluid 66 so far as obtaining the x-ray image is concerned. This also allows decreased x-ray dosage exposure to the patient 16 as compared to otherwise having the x-rays 24 penetrate the container 64 and/or fluid 66 en-route to the x-ray detector 26, as well as freeing the x-ray imaging system and ultrasound imaging system from interfering with each other.

In addition, any or all of the motors 32, 68, 70 can be motor powered, hydraulic, and/or operative via other motive mechanisms, and they may also be combined and/or separated, as needed and/or desired.

Those skilled in the art will readily recognize that various adaptations and modifications can also be made to the inventive arrangements that will result in improved mammography for breast screening, yet all of which will fall within the spirit and scope of the inventive arrangements, as particularly defined in the following claims. Accordingly, the inventive arrangements are limited, if at all, only by the following claims and/or their equivalents.

What is claimed is:

1. A mammography system, comprising:
   a patient support having at least one opening therein;
   an x-ray source configured to transmit x-rays through, at least in part, a portion of at least one breast of a patient extending, at least in part, through the opening;
   an x-ray detector opposing the x-ray source and configured to receive the x-rays transmitted from the x-ray source to obtain, at least in part, an x-ray image of that portion of the breast;
   a mounting structure configured to rotate the x-ray source and x-ray detector at multiple rotational positions around the opening while the x-rays transmitted by the x-ray source impinge on the x-ray detector, and the x-ray source and x-ray detector maintain a fixed relation relative to one another;

a container configured to be filled, at least in part, with a fluid and positioned proximate to and aligned with the opening to receive, at least in part, that portion of the breast;

an ultrasound transmitter configured to transmit sound waves through, at least in part, that portion of the breast when positioned, at least in part, within the fluid; and an ultrasound receiver opposing the ultrasound transmitter and configured to receive the sound waves from the ultrasound transmitter to obtain, at least in part, an ultrasound image of that portion of the breast.

2. A mammography system, comprising:

a patient support having at least one opening therein;

an x-ray source configured to transmit x-rays through, at least in part, a portion of at least one breast of a patient extending, at least in part, through the opening;

an x-ray detector opposing the x-ray source and configured to receive the x-rays transmitted from the x-ray source to obtain, at least in part, an x-ray image of that portion of the breast;

a mounting structure configured to rotate the x-ray source and x-ray detector at multiple rotational positions around the opening while the x-rays transmitted by the x-ray source impinge on the x-ray detector, and the x-ray source and x-ray detector maintain a fixed relation relative to one another;

a container configured to be filled, at least in part, with a fluid and positioned proximate to and aligned with the opening to receive, at least in part, that portion of the breast;

an ultrasound transmitter configured to transmit sound waves through, at least in part, that portion of the breast when positioned, at least in part, within the fluid;

an ultrasound receiver opposing the ultrasound transmitter and configured to receive the sound waves from the ultrasound transmitter to obtain, at least in part, an ultrasound image of that portion of the breast; and a motive mechanism configured to position the ultrasound transmitter and/or ultrasound receiver at a first position when obtaining the x-ray image of the breast and a second position when obtaining the ultrasound image of the breast.

3. The system of claim 2, wherein the patient support is configured to support the patient, at least in part, when the patients lies thereon.

4. The system of claim 2, wherein the patient support is configured so that the breast extends, at least in part, gravitationally downward through the opening.

5. The system of claim 2, wherein the x-ray source and x-ray detector are positioned on opposing sides of the opening on a same side of the patient support.

6. The system of claim 2, wherein the x-ray source and x-ray detector are rotable together around the opening on a same side of the patient support.

7. The system of claim 2, wherein the container is movable with respect to the opening to receive the breast when the breast is positioned, at least in part, within the opening.

8. The system of claim 2, wherein the container is movable towards and/or away from the opening to receive the breast when the breast is positioned, at least in part, within the opening.

9. The system of claim 2, further comprising:
a same or additional motive mechanism configured to position the container around the opening on a same side of the patient support.

10. The system of claim 2, further comprising:
a same or additional motive mechanism configured to position the container around the opening on a same side of the patient support when the breast is positioned, at least in part, within the opening.

11. The system of claim 2, wherein the fluid is water.

12. The system of claim 2, wherein the fluid is an ultrasonic gel.

13. The system of claim 2, wherein the fluid is a soundwave conductive fluid or gel.

14. The system of claim 2, wherein the ultrasound transmitter and ultrasound receiver are located within an ultrasound probe.

15. The system of claim 2, wherein the ultrasound transmitter and ultrasound receiver are components of a common transducer.

16. The system of claim 2, wherein the ultrasound transmitter and ultrasound receiver are positioned on opposing sides of the opening and/or container on a same side of the patient support.

17. The system of claim 2, wherein either or both of the ultrasound transmitter and/or ultrasound receiver are movable with respect to the container when the breast is positioned, at least in part, within the container and/or fluid.

18. The system of claim 2, wherein either or both of the ultrasound transmitter and/or ultrasound receiver are movable towards and/or away from the container when the breast is positioned, at least in part, within the container and/or fluid.

19. The system of claim 2, wherein the first position is remote from the breast.

20. The system of claim 2, wherein the second position is proximate the breast.

21. The system of claim 2, wherein the first position is remote from the breast and the second position is proximate the breast.

22. A mammography method, comprising:

positioning a patient such that, at least in part, a portion of at least one breast of the patient extends, at least in part, through at least one opening in a patient support;

transmitting x-rays through, at least in part, that portion of the breast;

receiving the x-rays to obtain, at least in part, an x-ray image of that portion of the breast;

filing a container, at least in part, with a fluid and positioning it proximate to and aligned with the opening to receive, at least in part, that portion of the breast;

immersing the breast, at least in part, into the fluid;

transmitting sound waves through, at least in part, that portion of the breast when positioned, at least in part, within the fluid; and receiving the sound waves to obtain, at least in part, an ultrasound image of that portion of the breast.

23. The method of claim 22, wherein positioning comprises supporting the patient, at least in part, on the patient support.

24. The method of claim 22, wherein positioning comprises supporting the patient, at least in part, such that the breast extends, at least in part, gravitationally downward through the opening.

25. The method of claim 22, further comprising:
moving the container with respect to the opening to receive the breast when the breast is positioned, at least in part, within the opening.

26. The method of claim 22, further comprising:
moving the container towards and/or away from the opening to receive the breast when the breast is positioned, at least in part, within the opening.

27. The method of claim 22, wherein transmitting and/or receiving sound waves comprises transmitting and/or receiving sound waves from a position proximate the container.

28. The method of claim 22, wherein transmitting and/or receiving sound waves comprises transmitting and/or receiving sound waves from a position proximate the container when obtaining the ultrasound image.

29. The method of claim 22, wherein transmitting and/or receiving sound waves comprises transmitting and/or receiving sound waves from a position proximate the container as opposed to an alternative position remote from the container.

30. The method of claim 22, wherein transmitting and/or receiving sound waves comprises transmitting and/or receiving sound waves from a position proximate the container when obtaining the ultrasound image as opposed to an alternative position remote from the container.

31. The method of claim 22, wherein transmitting and/or receiving sound waves comprises transmitting and/or receiving sound waves from a position proximate the container when obtaining the ultrasound image as opposed to an alternative position remote from the container when obtaining the x-ray image.

* * * * *